United States Patent [19]

DeLuca et al.

[11] Patent Number: 5,276,061

[45] Date of Patent: Jan. 4, 1994

[54] COSMETIC COMPOSITIONS CONTAINING 1α-HYDROXYVITAMIN D HOMOLOGS

[75] Inventors: Hector F. DeLuca, Deerfield; Connie M. Smith, Madison, both of Wis.

[73] Assignee: Wisconsin Alumni Research Foundation, Madison, Wis.

[21] Appl. No.: 573,339

[22] Filed: Aug. 24, 1990

[51] Int. Cl.$^5$ ............................ A61K 7/48; A61K 9/06
[52] U.S. Cl. ..................... 514/844; 514/167; 514/458; 514/725; 514/846; 514/847; 514/855; 514/859; 514/861; 514/864; 514/886; 514/887; 514/969
[58] Field of Search ................ 514/847, 167; 552/653

[56] References Cited

U.S. PATENT DOCUMENTS

| Re. 33,107 | 11/1989 | Dikstein et al. | 514/46 |
|---|---|---|---|
| 4,230,701 | 10/1980 | Holick et al. | 514/167 |
| 4,610,978 | 9/1986 | Dikstein et al. | 514/46 |
| 4,717,721 | 1/1988 | DeLuca et al. | 514/167 |
| 4,728,643 | 3/1988 | Holick et al. | 514/167 |
| 4,800,198 | 1/1989 | DeLuca et al. | 514/167 |
| 4,847,012 | 7/1989 | DeLuca et al. | 260/397.2 |
| 4,851,401 | 7/1989 | DeLuca et al. | 514/167 |
| 4,927,815 | 5/1990 | DeLuca et al. | 514/167 |

FOREIGN PATENT DOCUMENTS

| 62-169711 | 7/1987 | Japan | 514/167 |
|---|---|---|---|
| 1-249714 | 10/1989 | Japan | 424/59 |

OTHER PUBLICATIONS

Chemical Abstracts, 1988, vol. 109, 98583y, Shimai et al.
Chemical Abstracts, 1989, vol. 110, 121059z, Matsugami et al.
Chemical Abstracts, 1987, vol. 107, 204952z.
Chemical Abstracts, 1985, vol. 102, 119659m.
Chemical Abstracts, 1990, vol. 113, 158449q, Abstract of Japanese 01249714.
Chemical Abstracts, 1990, vol. 113, 78822r Calverlay et al.
Kutner et al., *The Journal of Organic Chemistry*, 1988, vol. 53, pp. 3450-3457.

Primary Examiner—Dale R. Ore
Attorney, Agent, or Firm—Andrus, Sceales, Starke & Sawall

[57] ABSTRACT

Compositions containing 1α-hydroxyvitamin D homolog compounds in a suitable carrier and methods employing such compositions are disclosed for cosmetic uses in the treatment of various skin conditions such as lack of adequate skin firmness, wrinkles, dermal hydration and sebum secretion. Various formulations of the compositions including creams, lotions and ointments are disclosed for use topically, orally or parenterally in accordance with this invention.

45 Claims, 3 Drawing Sheets

COSMETIC COMPOSITIONS CONTAINING 1α-HYDROXYVITAMIN D HOMOLOGS

This invention was made with United States Government support awarded by the National Institute of Health. NIH #DK14881. The United States Government has certain rights in this invention.

BACKGROUND OF THE INVENTION

The present invention relates to cosmetic compositions, and more particularly to such compositions containing 1α-hydroxyvitamin D homolog compounds.

Skin problems range between severe skin disorders such as dermatitis, eczema, psoriasis, solar keratosis and the like, and less severe skin conditions such as wrinkles, lack of dermal hydration i.e. dry skin, lack of adequate skin firmness i.e. skin slackness, insufficient sebum secretion and the like. The former skin disorders have typically been treated wtih compositions termed "dermatological" whereas the latter skin conditions have typically been treated with compositions termed "cosmetic" since the primary functions of such compositions are to preserve, condition or protect the skin.

In the past, treatment of various skin disorders and skin conditions has been largely based on non-specific-drugs. For example, dermatitis has been commonly treated with corticosteroids. Such compounds may provide symptomatic relief for some patients. However, steroids are known to produce numerous local and systemic side effects, and their long term use is not recommended.

Holick et al U.S. Pat. No. 4,728,643 discloses a method of treating psoriasis by administering to a patient a Vitamin D compound capable of differentiating cultured tumor cells. Examples of such compounds are vitamins $D_2$ or $D_3$ or derivatives of vitamins $D_2$ or $D_3$.

Dikstein et al U.S. Pat. No. 4,610,978 and U.S. Reissue Pat. No. 33,107 disclose cosmetic and dermatological compositions containing 1 alpha-hydroxycholecalciferol or 1 alpha, 25-dihydroxycholecalciferol. These compositions are disclosed for use in the topical treatment of skin disorders and skin conditions such as dermatitis, psoriasis, eczema, solar keratosis, wrinkles, dry skin and skin slackness.

Japanese published patent application No. 62/169711 entitled "A Skin Cosmetic Material" discloses a skin cosmetic composition containing vitamin $D_3$ and/or vitamin $D_3$ derivatives. The vitamin $D_3$ derivatives disclosed include 25-hydroxycholecalciferol, 1 alpha-hydroxy-cholecalciferol, 5,6-trans-25-hydroxycholecalciferol, 1 alpha-25-dihydroxycholecalciferol and dihydrotachysterol.

SUMMARY OF THE INVENTION

Cosmetic compositions containing one or more 1α-hydroxyvitamin D homolog compounds and a suitable carrier useful in the treatment of various skin conditions are described. The treatment may be topical, oral or parenteral. Methods of employing the compositions are also disclosed. The compounds are present in the composition in an amount from about 0.001 μg/gm to about 10.0 μg/gm of the composition, and may be administered orally or parenterally in dosages of from about 0.1 μg/day to about 25 μg/day.

In one aspect of the invention, cosmetic compositions containing one or more side chain unsaturated 1α-hydroxyvitamin D homolog compounds for the treatment of skin conditions such as wrinkles, lack of dermal hydration i.e. dry skin, lack of adequate skin firmness i.e. slack skin, and insufficient sebum secretion are provided. Methods employing these cosmetic compositions are also provided.

In another aspect of the invention, cosmetic compositions containing one or more side chain saturated 1α-hydroxyvitamin D homolog compounds for the treatment of skin conditions such as wrinkles, lack of dermal hydration i.e. dry skin, lack of adequate skin firmness i.e. slack skin, and insufficient sebum secretion are provided. Methods employing these cosmetic compositions are also provided.

Various formulations for the cosmetic compositions are also provided. Such formulations may include creams, lotions, ointments, and the like. The compositions and/or formulations may also include additional active ingredients if desired.

The compounds disclosed herein unexpectedly provide highly effective treatments for the above skin conditions without producing unwanted systemic or local side effects.

DETAILED DESCRIPTION OF THE INVENTION

Figure 1:
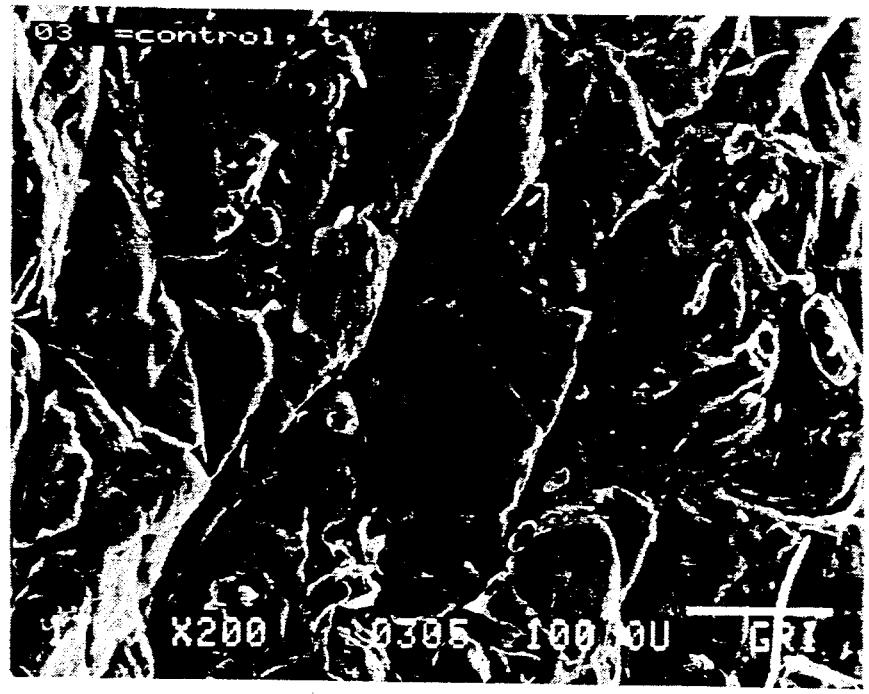
FIG. 1 is a photomicrograph at ×200 magnification of a skin replica of a control mouse treated topically with a propylene glycol control vehicle.

It has now been found that effective treatment of various skin conditions can be achieved with compositions which include an effective amount of a 1α-hydroxyvitamin D homolog compound.

The compounds useful in the cosmetic compositions of the present invention are characterized structurally as side chain unsaturated and side chain saturated homologs of vitamin D, and preferably of 1,25-$(OH)_2D_3$, in which the side chain is elongated by insertion of one or more methylene units into the chain at the carbon 24 position. They may be represented, therefore, by the following general structure;

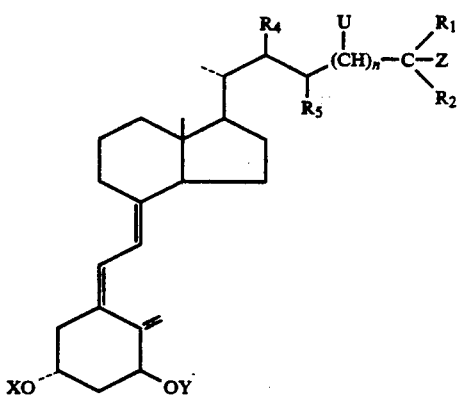

where $R_4$ and $R_5$ represent hydrogen or when taken together $R_4$ and $R_5$ represent a carbon-carbon double bond or a carbon-carbon triple bond, Z represents hydrogen, hydroxy or protected-hydroxy, U represents hydrogen, hydroxy, protected-hydroxy or an alkyl group, X and Y which may be the same or different are hydrogen or a hydroxy-protecting group, $R_1$ represents the group $-(CH_2)_q-H$ and $R_2$ represents the group $-(CH_2)_p-H$, and where n, q and p are integers having independently the values of 1 to 5 with the proviso that at least one of n, q and p is greater than 1, and $R_1$ and $R_2$ when taken together represent the group $-(CH_2)_m-$ where m is an integer having the value of 2 to 5.

As used in the description, and in the claims, the term "hydroxy-protecting group" refers to any group commonly used for the protection of hydroxy functions during subsequent reactions, including, for example, acyl or alkylsily groups such as trimethylsilyl, triethylsilyl, t-butyldimethylsilyl and analogous alkylated silyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings. "Alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl" and "fluoroalkyl" refer to such an alkyl radical substituted by one or more hydroxy or fluoro groups respectively. An acyl group is an alkanoyl group of 1 to 6 carbons in all its isomeric forms, or an aroyl group, such as benzoyl, or halo-, nitro- or alkyl- substituted benzoyl groups, or a dicarboxylic acyl group such as oxalyl, malonyl, succinoyl, glutaroyl, or adipoyl. The term "aryl" signifies a phenyl group.

It should be noted in this description that the term "24-dihomo" refers to the addition of two methylene groups at the carbon 24 position in the side chain. Likewise, the term "trihomo" refers to the addition of three methylene groups. Also, the term "26, 27-dimethyl" refers to the addition of a methyl group at the carbon 26 and 27 positions so that for example $R_1$ and $R_2$ are ethyl groups. Likewise, the term "26, 27-diethyl" refers to the addition of an ethyl group at the 26 and 27 positions so that $R_1$ and $R_2$ are propyl groups.

Specific and preferred examples of these compounds when the side chain is unsaturated (i.e. $R_4$ and $R_5$ represent a double bond) are: 24-dihomo-1, 25-dihydroxy-22-dehydrovitamin $D_3$, i.e. the compound shown above, where X and Y are hydrogen, Z is hydroxy, n equals 3, and $R_1$ and $R_2$ are each a methyl group; 26,27-dimethyl-24-dihomo-1,25-dihydroxy-22-dehydrovitamin $D_3$, i.e. the compound shown above where X and Y are hydrogen, Z is hydroxy, n equals 3, and $R_1$ and $R_2$ are each an ethyl group; 24-trihomo-1,25-dihydroxy-22-dehydrovitamin $D_3$, i.e. the compound having the structure shown above, where X and Y are hydrogen, Z is hydroxy, n equals 4, and $R_1$ and $R_2$ are each a methyl group; 26,27-dimethyl-24-trihomo-1,25-dihydroxy-22-dehydrovitamin $D_3$, i.e. the compound shown above where X and Y are hydrogen, Z is hydroxy, n equals 4, and $R_1$ and $R_2$ are each an ethyl group; 26,27-diethyl-24-dihomo-1,25-dihydroxy-22-dehydrovitamin $D_3$, i.e. the compound shown above where X and Y re hydrogen, Z is hydroxy, n equals 3, and $R_1$ and $R_2$ are each a propyl group; 26, 27-diethyl-24-trihomo-1,25-dihydroxy-22-dehydrovitamin $D_3$, i.e. the compound shown above where X and Y are hydrogen, Z is hydroxy, n equals 4, and $R_1$ and $R_2$ are each a propyl group; 26,27-dipropyl-24-dihomo-1,25-dihydroxy-22-dehydrovitamin $D_3$, i.e. the compound shown above where X and Y are hydrogen, Z is hydroxy, n equals 3, and $R_1$ and $R_2$ are each a butyl group; and 26,27-dipropyl-24-trihomo-1,25-dihydroxy-22-dehydrovitamin $D_3$, i.e. the compound shown above where X and Y are hydrogen, Z is hydroxy, n equals 4, and $R_1$ and $R_2$ are each a butyl group.

Specific and preferred examples of these compounds when the side chain is saturated (i.e. $R_4$ and $R_5$ each represent hydrogen) are: 24-dihomo-1,25-dihydroxyvitamin $D_3$, i.e. the compound shown above, where X and Y are hydrogen, Z is hydroxy, n equals 3, and $R_1$ and $R_2$ are each a methyl group; 26,27-dimethyl-24-dihomo-1,25-dihydroxy-vitamin $D_3$, i.e. the compound shown above where X and Y are hydrogen, Z is hydroxy, n equals 3, and $R_1$ and $R_2$ are each an ethyl group; 24-trihomo-1,25-dihydroxy-vitamin $D_3$, i.e. the compound having the structure shown above, where X and Y are hydrogen, Z is hydroxy, n equals 4, and $R_1$ and $R_2$ are each a methyl group; 26,27-dimethyl-24-trihomo-1,25-dihydroxy-vitamin $D_3$, i.e. the compound shown above where X and Y are hydrogen, Z is hydroxy, n equals 4, and $R_1$ and $R_2$ are each an ethyl group; 26, 27-diethyl-24-dihomo-1,25-dihydroxy-vitamin $D_3$, i.e. the compound shown above where X and Y are hydrogen, Z is hydroxy, n equals 3, and $R_1$ and $R_2$ are each a propyl group; 26,27-diethyl-24-trihomo-1,25-dihydroxy-vitamin $D_3$, i.e. the compound shown above where X and Y are hydrogen, Z is hydroxy, n equals 4, and $R_1$ and $R_2$ are each a propyl group; 26,27-dipropyl-24-dihomo-1,25-dihydroxy-vitamin $D_3$, i.e. the compund shown above where X and Y are hydrogen, Z is hydroxy, n equals 3, and $R_1$ and $R_2$ are each a butyl group; and 26,27-dipropyl-24-trihomo-1,25-dihydroxy-vitamin $D_3$, i.e. the compound shown above where X and Y are hydrogen, Z is hydroxy, n equals 4, and $R_1$ and $R_2$ are each a butyl group.

Preparation of Homologated Saturated and Unsaturated Side Chain Compounds

Examples of the compounds of this invention wherein the side chain is saturated can be prepared according to the general process illustrated and described in U.S. Pat. No. 4,927,815 issued May 22, 1990 entitled "Compounds Effective in Inducing Cell Differentiation And Process For Preparing Same", the description of which is specifically incorporated herein by reference. Examples of the compounds of this invention wherein the side chain is unsaturated can be prepared according to the general process illustrated and described in U.S. Pat. No. 4,847,012 issued Jul. 11, 1989 entitled "Vitamin D Related Compounds And Process For Their Preparation", the description of which is specifically incorporated herein by reference. Examples of the compounds of this invention wherein $R_1$ and $R_2$ together represent a cyclopentano group can be prepared according to the general process illustrated and described in U.S. Pat. No. 4,851,401 issued Jul. 25, 1989 entitled "Novel Cyclopentano-Vitamin D Analogs", the description of which is specifically incorporated herein by reference.

Another synthetic strategy for the preparation of side-chain-modified analogues of $1\alpha,25$-dihydroxycholecalciferol and $1\alpha,25$-dihydroxyergocalciferol is disclosed in Kutner et al, *The Journal of Organic Chemistry*, 1988, Vol. 53, pages 3450–3457. In addition, the preparation of 24-homo and 26-homo vitamin D analogs is disclosed in U.S. Pat. No. 4,717,721 issued Jan. 5, 1988 entitled "Sidechain Homo-Vitamin D Compounds With Preferential Anti-Cancer Activity," the description of which is specifically incorporated herein by reference.

In accordance with the present invention, the above side chain saturated and unsaturated $1\alpha$-hydroxyvitamin D homolog compounds are employed in cosmetic compositions, formulations thereof and methods of using for the treatment of such skin conditions as dry skin (lack of dermal hydration), undue skin slackness (i.e., insufficient skin firmness) and insufficient sebum secretion. The cosmetic compositions are also effective in the general preservation, conditioning and protecting of the skin, e.g., against wrinkles.

Cosmetic compositions for use in the above-mentioned treatment of skin comprise a cosmetically effective amount of one or more side chain unsaturated or side chain saturated $1\alpha$-hydroxyvitamin D homolog compound as the active ingredient and a suitable carrier. A cosmetically effective amount of such compounds for use in accordance with this invention is from about 0.001 $\mu$g to about 10.0 $\mu$g per gm of composition, and may be administered orally or parenterally in dosages of from about 0.1 $\mu$g/day to about 25 $\mu$g/day. A concentration of 0.01 $\mu$g per gm of the composition is preferred.

The cosmetic compositions of this invention are formulated preferably as creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers and antioxidants may also be included as well as agents imparting color or fragrance if desired.

Cosmetic creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Cosmetic ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Cosmetic lotions may be conveniently prepared by dissolving the active ingredient, in a suitable high molecular weight alcohol such as propylene glycol or polyethylene glycol.

One or more additional substances which have therapeutic effects on the skin may also be incorporated in the cosmetic compositions. Thus in one embodiment of this invention the composition also contains one or more compounds capable of increasing cyclic-AMP levels in the skin. Suitable compounds include adenosine or a nucelic acid hydrolysate in an amount of about 0.1–1% and papaverine, in an amount of about 0.5–5%, both by weight based on the weight of the composition. Also suitable are $\beta$-adrenergic agonists such as isoproterenol, in an amount of about 0.1–2% or cyclic-AMP, in an amount of about 0.1–1%, again both by weight based on the weight of the composition. Other suitable types of additional active ingredients which may be incorporated in the compositions of this invention include any compounds known to have a beneficial effect on skin. Such compounds include retinoids such as Vitamin A, in an amount of about 0.003%–0.3% by weight and chromanols such as Vitamin E or a derivative thereof in an amount of about 0.1–10% by weight, both based on the weight of the composition. Additionally, anti-inflammatory agents and keratoplastic agents may be incorporated in the cosmetic composition. A typical anti-inflammatory agent is a corticosteroid such as hydrocortisone or its acetate in an amount of about 0.25–5% by weight, or a corticosteroid such as dexamethasone in an amount of about 0.025–0.5% by weight, both based on the weight of the composition. A typical keratoplastic agent is coal tar in an amount of about 0.1–20% or anthralin in an amount of about 0.05–2% by weight, both based on the weight of the composition.

Topical application and intraperitoneal injection of cosmetic compositions of this invention was found to be cosmetically effective in field studies. In a typical example, topical application of a lotion containing 0.01 $\mu$g of $1\alpha$-hydroxyvitamin D homolog compound per gram of lotion to the skin of nude mice for five weeks resulted in improved skin condition.

The cosmetic efficacy of compositions containing $1\alpha$-hydroxyvitamin D homolog compounds in accordance with this invention was determined by the following procedures:

Two treatment groups of six mice each were available with Group I being controls and Group II being the treatment group with Trihomo-$D_3$. Three mice in each group received the treatment topically (t) and three mice received it intraperitoneally (ip) three times a week for about 5 weeks. By visual evaluation, the mice treated with the Trihomo-$D_3$ compound (b) had the pinkest, smoothest skin as compared to the control mice.

Replicas were made about 48 hours after the last treatment of the backs of 5 control animals and 4 experimental animals. Silflo ™ silicone rubber was spread onto the rear half of each mouse back (anesthetized with diethyl ether) and allowed to polymerize for 5 to 7 minutes. These silicone rubber "negative" replicas were stored in glassine envelopes until polyethylene "positive" replicas were made. The procedures for preparing both the negative and the positive replicas will hereinafter be described.

The nine positive replicas were coated with 60 nm gold and examined in a JEOL JSM-35C scanning electron microscope at 15 kV accelerating voltage. Differences between replicas were evident to the unaided eye and from Polaroid micrographs made of each replica at ×12 to form a montage of the entire surface. Micrographs were also made at ×100 and ×200 to differentiate fine details of skin surface condition.

Figure 2:
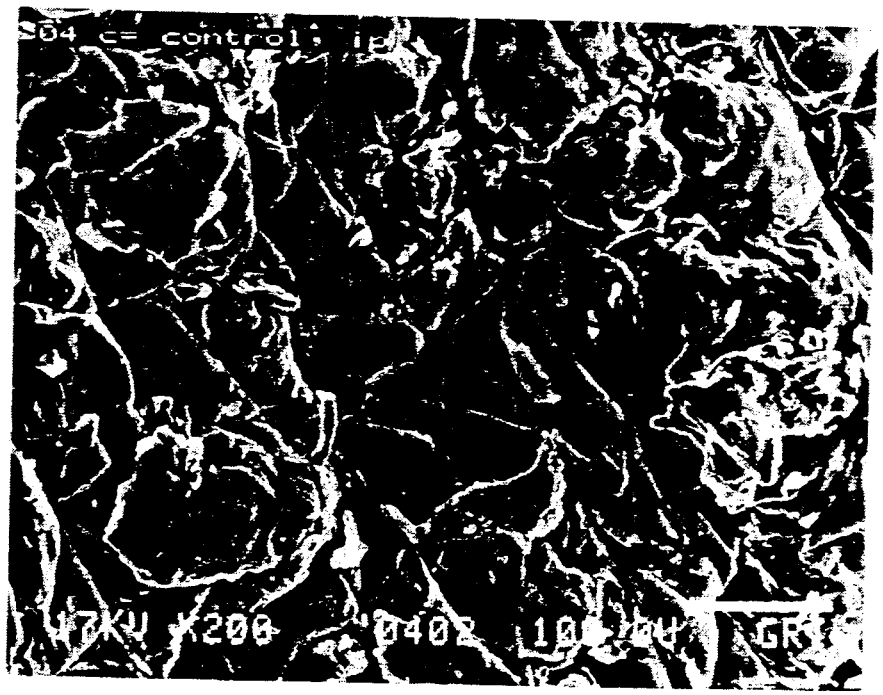
FIG. 2 is a photomicrograph at ×200 magnification of a skin replica of a second control mouse treated intraperitoneally with a propylene glycol control vehicle.
Figure 3:
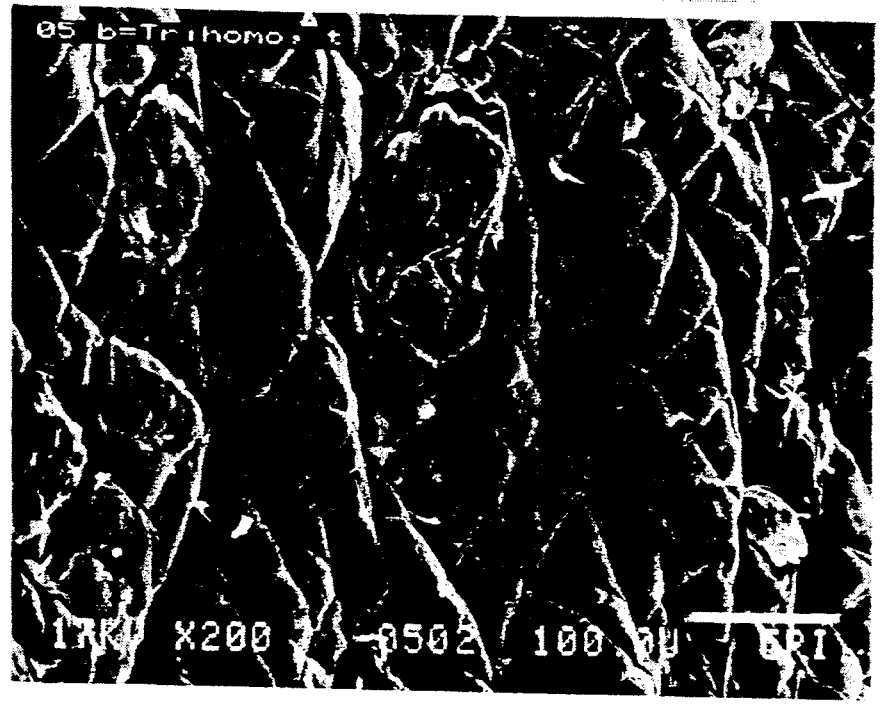
FIG. 3 is a photomicrograph at ×200 magnification of a skin replica of an experimental mouse treated topically with $\Delta^{22}$, 24, 24, 24-trihomo-1α, 25-dihydroxyvitamin $D_3$.
Figure 4:
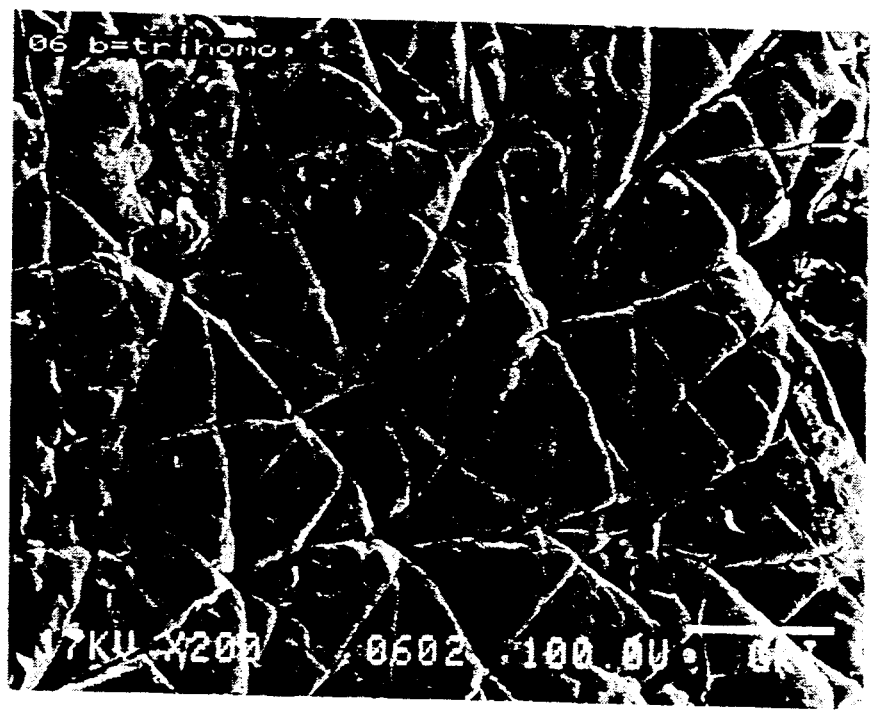
FIG. 4 is a photomicrograph at ×200 magnification of a skin replica of a second experimental mouse treated topically with $\Delta^{22}$, 24,24,24-trihomo-1α,25-dihydroxyvitamin $D_3$.
Figure 5:
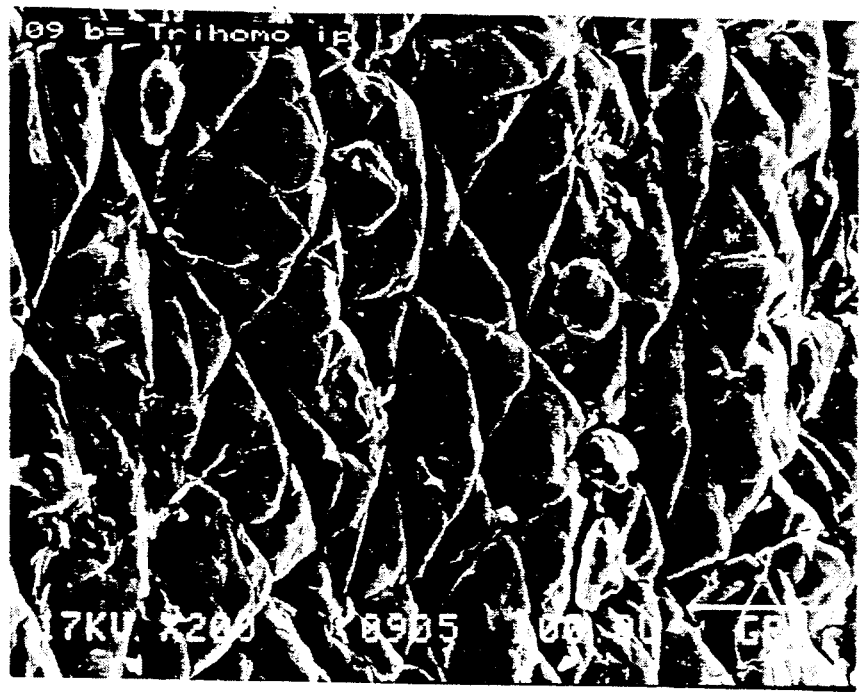
FIG. 5 is a photomicrograph at ×200 magnification of a skin replica of an experimental mouse treated intraperitoneally with $\Delta^{22}$, 24, 24, 24-trihomo-1α,25-dihydroxyvitamin $D_3$.
Figure 6:
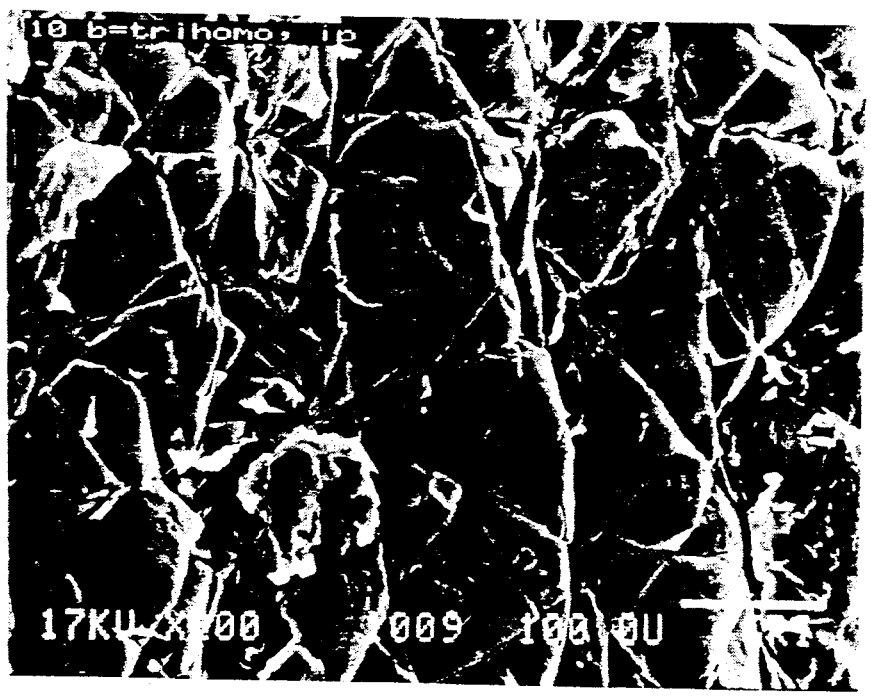
FIG. 6 is a photomicrograph at ×200 magnification of a skin replica of a second experimental mouse treated intraperitoneally with $\Delta^{22}$, 24, 24, 24-trihomo-1α,25-dihydroxy vitamin $D_3$.

FIGS. 1 and 2 illustrate the skin surface condition of two of the control mice treated topically and intraperitoneally with a propylene glycol vehicle only. FIGS. 3 and 4 illustrate the skin condition of two of the experimental mice treated topically with $\Delta^{22}$, 24, 24, 24-thihomo-1α,25-dihydroxyvitamin $D_3$ (Trihomo $D_3$), whereas FIGS. 5 and 6 illustrate the skin condition of two of the experimental mice treated intraperitoneally with $\Delta^{22}$, 24,24,24-trihomo-1α, 25-dihydroxyvitamin $D_3$.

The results of the above experiments were that the low magnification (×12) montages of the nine skin replicas could be ranked into four groups according to visible wrinkling and overall skin surface roughness. The best skin condition (rank 1) was exhibited by samples #5, #6, and #8, all of which were treated with Trihomo-$D_3$. The next best was #7. The third rank included three of the control samples. The remaining two controls could be placed alone in a fourth rank having the roughest skin (Table 1).

Details of the skin surface rich as stratum corneum desquamation, scaling, size and plumpness of skin divisions, were visible on higher magnification (×100 and ×200) micrographs and used to rank the replicas from 1=best skin to 6=worst skin (Tables 1 and 2). The treated samples ranked 1 to 4, and the five controls ranked 5 and 6. The top-ranked four included all of the Trihomo-$D_3$ samples (#5, #6, #7, #8). There was no discernible difference between topical and intraperitoneal Trihomo-$D_3$, i.e. #6, #7, #8 were very nearly equal in appearance.

As a result of these experiments, it may be concluded that topical and intraperitoneal treatments of nude mice with 1α-hydroxy Vitamin D analogs produce visible changes in skin surface condition as seen on replicas. Treated samples showed less gross wrinkling and scaling and more smooth, plump, rounded skin microtopography than the respective controls. Treatment with Trihomo-$D_3$ clearly had a greater effect than no treatment at all. Topical treatment could not be differentiated from intraperitoneal treatment.

TABLE 1

| SEM OF MOUSE SKIN REPLICAS | | | |
|---|---|---|---|
| No. | Treatment | Rank* (X12) | Rank* (X100, 200) |
| #1 | c-t control | 3 | 6 |
| #2 | c-t control | 4 | 6 |
| #3 | c-t control | 3 | 6 |
| #4 | c-ip control | 3 | 6 |
| #5 | b-t Trihomo-$D_3$ | 1 | 4 |
| #6 | b-t Trihomo-$D_3$ | 1 | 1 |
| #7 | b-ip Trihomo-$D_3$ | 2 | 2 |
| #8 | b-ip Trihomo-$D_3$ | 1 | 3 |
| #9 | c-ip control | 4 | 5 |

Treatments:
b = Trihomo-$D_3$
c = Control, vehicle only
t = topical, 160 ng Trihomo-$D_3$/20 μl propylene glycol applied 3 times per week
ip = intraperitoneal, 50 ng Trihomo-$D_3$/50μl propylene glycol given 3 times per week

TABLE 2

| RANKING OF MOUSE SKIN REPLICAS | | |
|---|---|---|
| Rank* | Treatment | Rank @ (X12) |
| 1 | #6 b-t | 1 |
| 2 | #7 b-ip | 2 |
| 3 | #8 b-ip | 1 |
| 4 | #5 b-t | 1 |
| 5 | #9 c-ip | 4 |
| 6 | #1 c-t | 3 |
| 6 | #2 c-t | 4 |
| 6 | #3 c-t | 3 |
| 6 | #4 c-ip | 3 |

*Scanning electron micrographs at X100 and X200 were judged for skin condition and ranked, with 1 = best (smoothest, plumpest, least scaling) and 6 = worst (roughest, most scaling).
@ Photo montages at X12 magnification were made of each 25 mm diameter replica and ranked for skin condition, with 1 = best (smoothest) and 4 = worst (roughest, more wrinkled).
Treatments:
b = Trihomo-$D_3$
c = Control, vehicle only
t = topical
ip = intraperitoneal The skin replication techniques utilized in preparing the "negative" and "positive" replicas in order to perform the above described experiments and the photomicrographs of FIGS. 1–6 will now be described.

A. SILFLO NEGATIVE REPLICAS

1. Mix Silflo well before dispensing. Put Silflo into plastic syringe, 5 or 10 ml size.
2. Measure out 0.4 to 0.8 ml onto glassine paper or small weighing dish. The amount depends on the area to be replicated and the rate of polymerization desired.
3. Add 1 drop thinner per 0.4 ml Silflo. (Steps 1-3 can be done in advance.)
4. Place TCOM adhesive ring on skin site(s) to be replicated. (This ring was omitted on the mice.)
5. Add 1 drop catalyst per 0.4 ml Silflo and start timer. These amounts can be adjusted if replica sets too fast or too slowly. Silflo should not stiffen until ~2 min. after catalyst addition and should set tack-free 3~3.5 min. after catalyst.
6. Mix thoroughly with spatula tip for 20-25 sec.
6a. To remove air bubbles, place Silflo dish into small vacuum desiccator and evacuate with mechanical pump until silicone rubber foams up once and collapses; remove at once from vacuum and apply to skin. (Elapsed time should be ~1 min. since addition of catalyst.)
7. Spread Silflo mixture quickly onto skin site with spatula.
8. Let Silflo set for a minimum of 5 minutes, without any movement of the subject. Check that the replica has polymerized before proceeding.
9. Peel off the replica and place it in a dust and lint-free container.

B. Polyethylene Positive Replicas

1. Allow Silflo replicas to polymerize completely at room temperature, usually overnight, but 6 hours is sufficient.
2. Place replicas in a dish such as glass petri dish, aluminum weighing dish or on a metal tray. Place a shallow brass ring (or other retaining device which serves as a mold for the polyethylene) on the replica. The diameter of the ring mold will depend on the diameter of the SEM specimen carrier being used (usually 15 mm or 25 mm).

3. Place replicas into 160°~170° C. oven for a short time, ~5 min. This heating of the replicas drives off moisture and other volatiles.
4. Remove replicas from oven. Fill each brass ring mold with polyethylene pellets.
5. Replace replicas in oven and heat until polyethylene has melted completely and covers the replica surface (~15 min.).
6. Turn oven off, open oven door and allow replicas to cool slowly. Too rapid cooling can cause cracks and artifacts in the polyethylene.
7. When replicas have cooled almost to room temperature, they can be removed from the oven. Peel off the Silflo replica from the polyethylene replica, which remains within its metal ring.
8. The hardened polyethylene replica can be sputter-coated with gold and examined in the SEM without removing it from its brass ring mold. The replica can also be pushed out of the ring mold and replaced in its again, if necessary.

The visible changes in skin surface condition (as shown in FIGS. 3-6 versus FIGS. 1-2), is in marked contrast with that of compositions containing ergocalciferol or cholecalciferol. Topical application of compositions containing ergocalciferol, for instance, were of low cosmetic efficacy and in fact resulted in decreased skin elasticity (See Table I in Dikstein et al U.S. Reissue No. 33,107). Moreover, since it is known that ergocalciferol and cholecalciferol are absorbed into the bloodstream through the skin, it is likely that doses of such compounds applied to large areas of the skin or applied chronically, even in the minimal active dose, cause systemic effects. Further, the compounds of the present invention demonstrated no expected or observed side effects.

We claim:

1. A cosmetic composition or the treatment of the skin conditions of skin slackness, wrinkles, dry skin and insufficient sebum secretion, which comprises an effective amount of a compound of the formula:

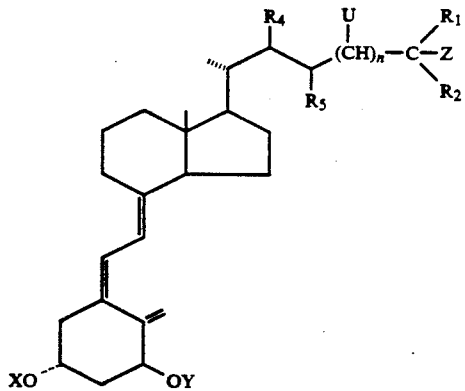

where $R_4$ and $R_5$ represent hydrogen or when taken together $R_4$ and $R_5$ represent a carbon-carbon double bond or a carbon-carbon triple bond. Z represents hydrogen, hydroxy, O-acyl, O-alkylsilyl, or O-alkoxyalkyl, U represents hydrogen, hydroxy, O-acyl, O-alkylsilyl, O-alkoxyalkyl or an alkyl group, X and Y which may be the same or different, are hydrogen or a hydroxy-protecting group, said hydroxy-protecting group comprising an acyl, alkylsilyl or alkoxyalkyl group, $R_1$ represents the group $-(CH_2)_q-H$ and $R_2$ represents the group $-(CH_2)_p-H$, and where n, q and p are integers having independently the values of 1 to 5 with the proviso that at least one of n, q and p is greater than 1, and $R_1$ and $R_2$ when taken together represent the group $-(CH_2)_m-$ where m is an integer having the value of 2 to 5, said effective amount comprising between about 0.001 µg to about 10.0 µg of said compound per gram of the composition, and a cosmetically acceptable topical carrier for said compound.

2. A cosmetic composition according to claim 1 wherein the compound is 24-dihomo-1α,25-dihydroxy-22-dehydrovitamin $D_3$.

3. A cosmetic composition according to claim 1 wherein the compound is 24-trihomo-1α,25-dihydroxy-22-dehydrovitamin $D_3$.

4. A cosmetic composition according to claim 1, wherein the compound is 26,27-dimethyl-24-dihomo-1α,25-dihydroxy-22-dehydrovitamin $D_3$.

5. A cosmetic composition according to claim 1, wherein the compound is 26,27-dimethyl-24-trihomo-1α,25-dihydroxy-22-dehydrovitamin $D_3$.

6. A cosmetic composition according to claim 1, wherein the compound is 26,27-diethyl-24-dihomo-1α,25-dihydroxy-22-dehydrovitamin $D_3$.

7. A cosmetic composition according to claim 1, wherein the compound is 26,27-diethyl-24-diethyl-24-trihomo-1α,25-dihydroxy-22-dehydrovitamin $D_3$.

8. A cosmetic composition according to claim 1, wherein the compound is 26,27-dipropyl-24-dihomo-1α,25-dihydroxy-22-dehydrovitamin $D_3$.

9. A cosmetic composition according to claim 1, wherein the compound is 26,27-dipropyl-24-trihomo-1α,25-dihydroxy-22-dehydrovitamin $D_3$.

10. A cosmetic composition according to claim 1, wherein the compound is present in the composition in an amount from about 0.001 µg/gm to about 0.03 µg/gm of the composition.

11. A cosmetic composition according to claim 1, wherein the compound is present in the composition in an amount from about 0.03 µg/gm to about 10.0 µg/gm of the composition.

12. A cream comprising a cosmetic composition according to claim 1, wherein the cosmetically acceptable topical carrier comprises a mixture of water, self-emulsifying beeswax, mineral oil and almond oil.

13. A cream according to claim 12, wherein the mixture includes in the following proportions:
water, about 40 parts;
self-emulsifying beeswax, about 20 parts;
mineral oil, about 40 parts; and
almond oil, about 1 part.

14. An ointment comprising a cosmetic composition according to claim 1, wherein the cosmetically acceptable topical carrier comprises a mixture of vegetable oil and white soft paraffin.

15. An ointment according to claim 14, wherein the vegetable oil is almond oil which is present in the amount of about 30% and the white soft paraffin is present in the amount of about 70%, both on the basis of weight.

16. A lotion comprising a cosmetic composition according to claim 1, wherein the cosmetically acceptable topical carrier comprises propylene glycol.

17. A cosmetic composition according to claim 1 which further comprises an effective amount of a retinoid.

18. A cosmetic composition according to claim 17, wherein the retinoid is Vitamin A and the effective amount is about 0.003–0.3% by weight based on the weight of the composition.

19. A composition according to claim 10, wherein the compound is a chromanol.

20. A composition according to claim 19, wherein the chromanol is Vitamin E and the effective amount is about 0.1–10% by weight based on the weight of the composition.

21. A cosmetic composition according to claim 1 wherein the compound is 24-dihomo-1α,25-dihydroxyvitamin $D_3$.

22. A cosmetic composition according to claim 1 wherein the compound is 24-trihomo-1α,25-dihydroxyvitamin $D_3$.

23. A cosmetic composition according to claim 1 wherein the compound is 26,27-dimethyl-24-dihomo-1α,25-dihydroxyvitamin $D_3$.

24. A cosmetic composition according to claim 1 wherein the compound is 26,27-dimethyl-24-trihomo-1α,25-dihydroxyvitamin $D_3$.

25. A cosmetic composition according to claim 1 wherein the compound is 26,27-diethyl-24-dihomo-1α,25-dihydroxyvitamin $D_3$.

26. A cosmetic composition according to claim 1 wherein the compound is 26,27-diethyl-24-trihomo-1α,25-dihydroxyvitamin $D_3$.

27. A cosmetic composition according to claim 1 wherein the compound is 26,27-dipropyl-24-dihomo-1α,25-dihydroxyvitamin $D_3$.

28. A cosmetic composition according to claim 1 wherein the compound is 26,27-dipropyl-24-trihomo-1α,25-dihydroxyvitamin $D_3$.

29. A method for treating the skin conditions of skin slackness, wrinkles, dry skin and insufficient sebum secretion which comprises topically applying to skin a cosmetically acceptable topical composition having an effective amount of a compound of the formula:

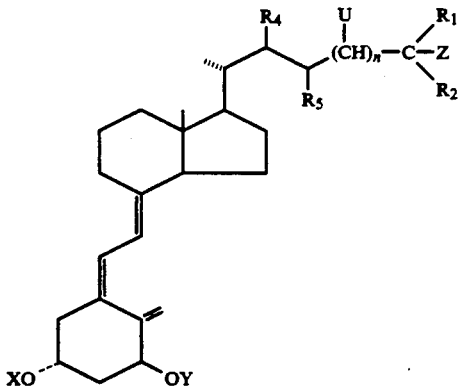

where $R_4$ and $R_5$ represent hydrogen or when taken together $R_4$ and $R_5$ represent a carbon-carbon double bond or a carbon-carbon triple bond, Z represents hdyrogen, hydroxy, O-acyl, O-alkylsilyl, or O-alkoxyalkyl, U represents hydrogen, hydroxy, O-acyl, O-alkylsily, O-alkoxyalkyl or an alkyl group, X and Y which may be the same or different, are hydrogen or a hydroxy-protecting group, said hydroxy-protecting group comprising an acyl, alkylsilyl or alkoxyalkyl group, $R_1$ represents the group—$(CH_2)_q$—H and $R_2$ represents the group —$(CH_2)_p$—H and where n, q and p are integers having independently the values of 1 to 5 with the proviso that at least one of n, q and p is greater than 1, and $R_1$ and $R_2$ when taken together represent the group —$(CH_2)_m$—where m is an integer having the value of 2 to 5, said effective amount comprising between about 0.001 μg to about 10.0 μg of said compound per gram of the composition.

30. The method of claim 29 wherein the compound is 24-dihomo-1α,25-dihydroxy-22-dehydrovitamin $D_3$.

31. The method of claim 29 wherein the compound is 24-trihomo-1α,25-dihydroxy-22-dehydrovitamin $D_3$.

32. The method of claim 29 wherein the compound is 26,27-dimethyl-24-dihomo-1α,25-dihydroxy-22-dehydrovitamin $D_{3l}$.

33. The method of claim 29 wherein the compound is 26,27-dimethyl-24-trihomo-1α,25-dihydroxy-22-dehydrovitamin $D_3$.

34. The method of claim 29 wherein the compound is 26,27-diethyl-24-dihomo-1α,25-dihydroxy-22-dehydrovitamin $D_3$.

35. The method of claim 29 wherein the compound is 26,27-dimethyl-24-trihomo-1α,25-dihydroxy-22-dehydrovitamin $D_3$.

36. The method of claim 29 wherein the compound is 26,27-dipropyl-24-dihomo-1α,25-dihydroxy-22-dehydrovitamin $D_3$.

37. The method of claim 29 wherein the compound is 26,27-diprohyl-24-trihomo-1α,25-dihydroxy-22-dehydrovitamin $D_3$.

38. The method of claim 29 wherein the compound is 24-dihomo-1α,25-dihydroxyvitamin $D_3$.

39. The method of claim 29 wherein the compound is 24-trihomo-1α,25-dihydroxyvitamin $D_3$.

40. The method of claim 29 wherein the compound is 26,27-dimethyl-24-dihomo-1α,25-dihydroxy-vitamin $D_3$.

41. The method of claim 29 wherein the compound is 26,27-dimethyl-24-trihomo-1α,25-dihydroxy-vitamin $D_3$.

42. The method of claim 29 wherein the compound is 26,27-diethyl-24-dihomo-1α, 25-dihydroxy-vitamin $D_3$.

43. The method of claim 29 wherein the compound is 26,27-dimethyl-24-trihomo-1α,25-dihydroxy-vitamin $D_3$.

44. The method of claim 29 wherein the compound is 26,27-dipropyl-24-dihomo-1α,25-dihydroxy-vitamin $D_3$.

45. The method of claim 29 wherein the compound is 26,27-dipropyl-24-trihomo-1α,25-dihydroxy-vitamin $D_3$.

* * * * *

UNITED STATES PATENT AND TRADEMARK OFFICE
CERTIFICATE OF CORRECTION

PATENT NO. : 5,276,061
DATED : January 4, 1994
INVENTOR(S) : HECTOR F. DELUCA ET AL It is certified that error appears in the above-identified patent and that said Letters Patent is hereby corrected as shown below:

| | |
|---|---|
| Claim 1, column 9, line 37: | Delete "or" and substitute therefore ---for---. |
| Claim 1, column 9, line 60: | Delete "." and substitute therefore ---,---. |
| Claim 7, column 10, line 27: | After "diethyl-24-", delete "diethyl-24-". |
| Claim 29, column 12, line 2: | Delete "O-alkylsily" and substitute therefore ---O-alkylsilyl---. |
| Claim 32, column 12, line 22: | Delete "$D_{31}$" and substitute therefore ---$D_3$---. |

Signed and Sealed this

Seventh Day of June, 1994

BRUCE LEHMAN

*Attest:*

*Attesting Officer*     Commissioner of Patents and Trademarks